(12) United States Patent
Baldauf et al.

(10) Patent No.: US 11,571,520 B2
(45) Date of Patent: Feb. 7, 2023

(54) PLUNGER ROD COMPRISING AT LEAST THREE ANNULAR ELEMENTS FOR A PREFILLED SYRINGE

(71) Applicant: Fresenius Kabi Austria GmbH, Graz (AT)

(72) Inventors: Wolfgang Baldauf, Fernitz (AT); Jörg Heinrich, Grünwald (DE); Christoph Zauner, Hausmannstätten (AT)

(73) Assignee: Fresenius Kabi Austria GmbH, Graz (AT)

( * ) Notice: Subject to any disclaimer, the term of this patent is extended or adjusted under 35 U.S.C. 154(b) by 354 days.

(21) Appl. No.: 16/752,784

(22) Filed: Jan. 27, 2020

(65) Prior Publication Data

US 2020/0155765 A1    May 21, 2020

Related U.S. Application Data

(63) Continuation of application No. 15/555,220, filed as application No. PCT/EP2016/054351 on Mar. 2, 2016, now Pat. No. 10,543,319.

(30) Foreign Application Priority Data

Mar. 2, 2015 (EP) .................................... 15000587

(51) Int. Cl.
 *A61M 5/31* (2006.01)
 *A61M 5/315* (2006.01)
 (Continued)

(52) U.S. Cl.
 CPC ........ *A61M 5/31515* (2013.01); *A61M 5/002* (2013.01); *A61M 5/28* (2013.01);
 (Continued)

(58) Field of Classification Search
 CPC .... A61M 5/31515; A61M 5/002; A61M 5/28; A61M 2205/581; A61M 5/31511; A61M 2005/3126; B65D 75/366
 See application file for complete search history.

(56) References Cited

U.S. PATENT DOCUMENTS

| 7,708,719 B2 | 5/2010 | Wilmot et al. |
| 9,433,729 B2 | 9/2016 | Ingram et al. |

(Continued)

FOREIGN PATENT DOCUMENTS

| CN | 102639174 B | 4/2014 |
| EP | 2484393 | 8/2012 |

(Continued)

*Primary Examiner* — Amber R Stiles
(74) *Attorney, Agent, or Firm* — Occhiuti & Rohlicek LLP

(57) ABSTRACT

A prefilled syringe includes a syringe body filled with a medical fluid, which has a nozzle at a front side, the nozzle being closed with a cap, and which is closed at a rear side with a displaceable plunger; and a plunger rod that can be inserted into the syringe body via the rear side. The plunger rod has a connecting portion at a front side, via whi9ch the plunger rod can be connected to the plunger. At least three annular elements, which extend at least in some sections about a longitudinal axis of the rod, are arranged on a rear side of the connecting portion on the plunger rod in such a manner that they are located in the syringe body when the plunger rod is fully connected to the plunger. The three annular elements support a coaxial connection of the rod to the plunger positioned in the syringe.

22 Claims, 5 Drawing Sheets

Figure 3:
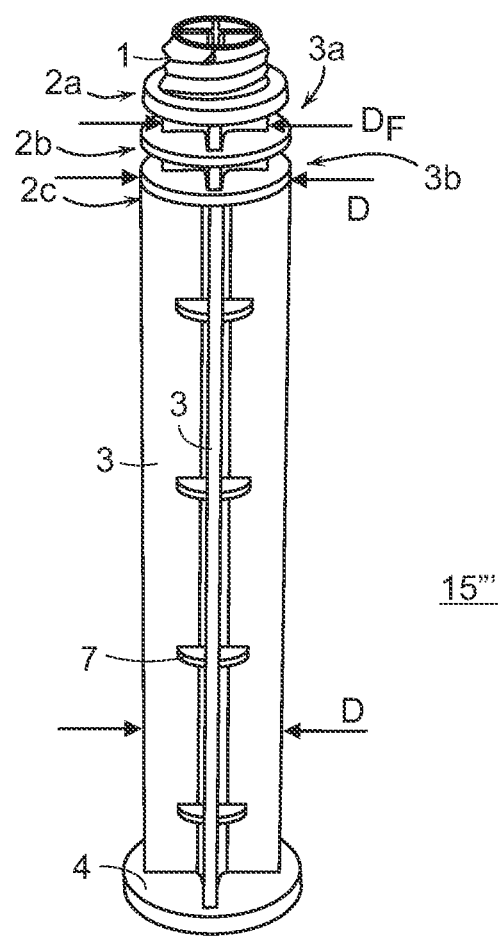

(51) Int. Cl.
*A61M 5/28* (2006.01)
*A61M 5/00* (2006.01)
*B65D 75/36* (2006.01)

(52) U.S. Cl.
CPC ....... *B65D 75/366* (2013.01); *A61M 5/31511* (2013.01); *A61M 2005/3126* (2013.01); *A61M 2205/581* (2013.01)

(56) References Cited

U.S. PATENT DOCUMENTS

| | | | |
|---|---|---|---|
| 10,543,319 B2 * | 1/2020 | Baldauf | A61M 5/28 |
| 2010/0181218 A1 * | 7/2010 | Beccaro | A61L 2/07 604/218 |
| 2012/0136298 A1 * | 5/2012 | Bendix | A61M 5/31515 29/428 |
| 2014/0207098 A1 * | 7/2014 | Ingram | A61M 5/31511 604/152 |
| 2016/0166772 A1 | 6/2016 | Mirzazadeh et al. | |

FOREIGN PATENT DOCUMENTS

| | | |
|---|---|---|
| JP | 2002-272843 | 9/2002 |
| JP | 2010246842 A | 11/2010 |
| JP | 4602579 B2 | 12/2010 |
| JP | 2011-072394 | 4/2014 |
| JP | 5634695 B2 | 12/2014 |
| WO | 2001/097885 | 12/2001 |
| WO | 0197885 A1 | 12/2001 |
| WO | 2004101016 A1 | 11/2004 |
| WO | 2010139793 A1 | 12/2010 |
| WO | 2014/053560 | 4/2014 |

\* cited by examiner

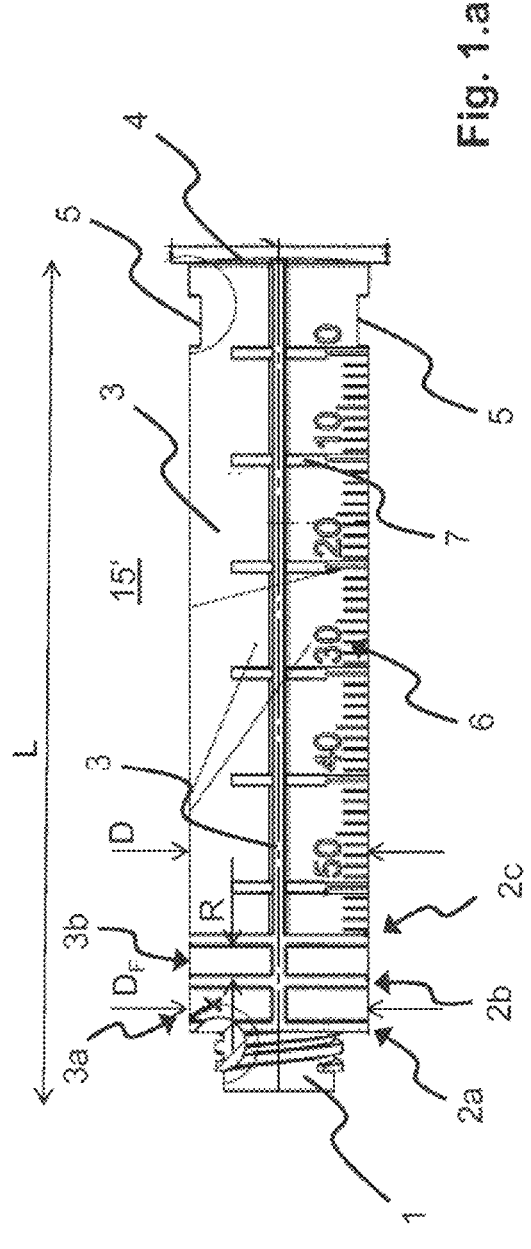
Fig. 1.a
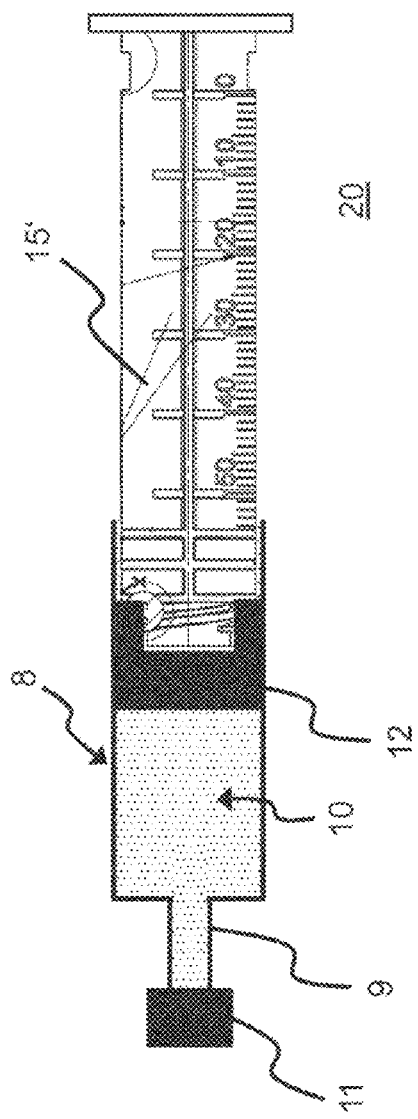
Fig. 1.b

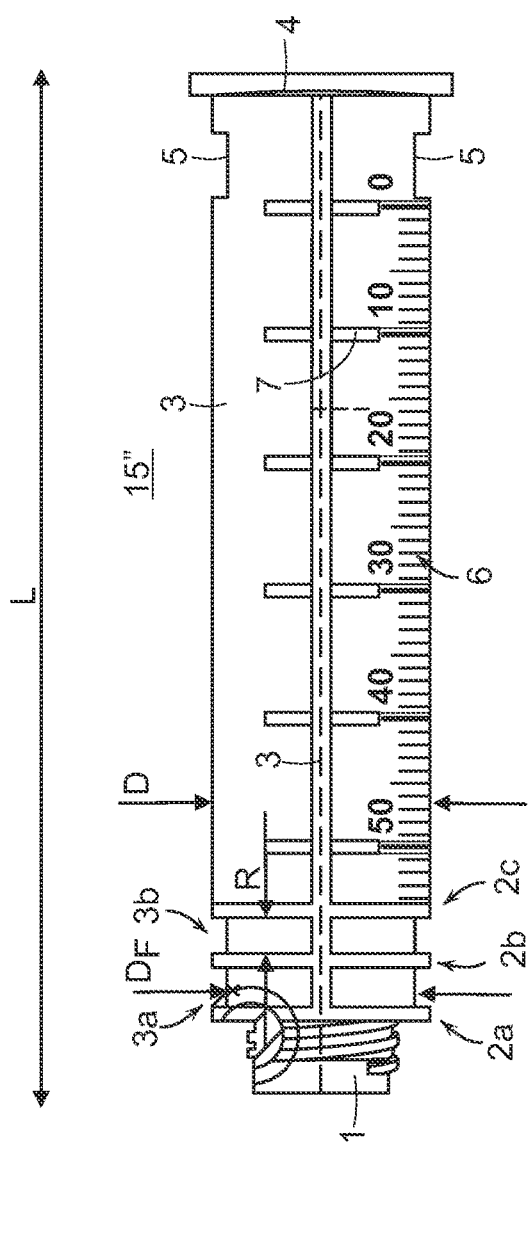
FIG. 2.a
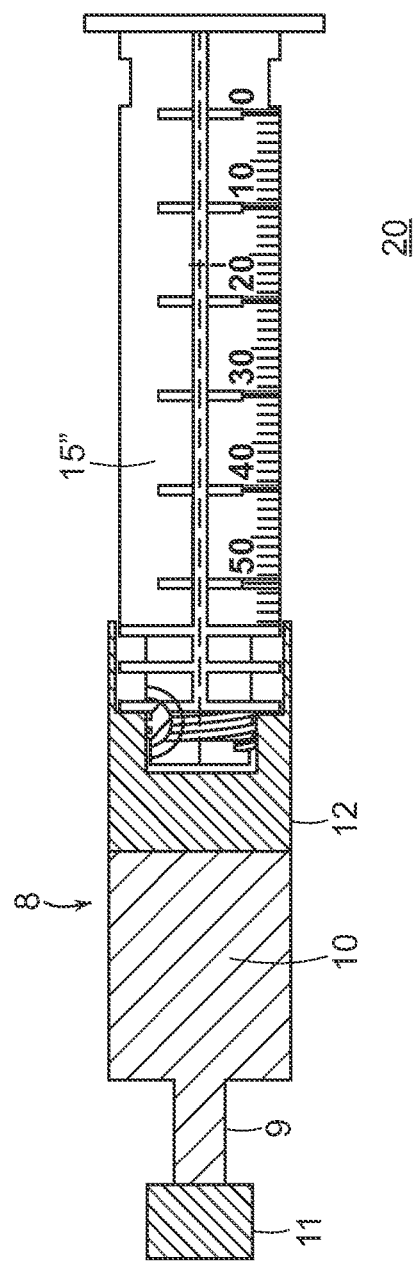
FIG. 2.b

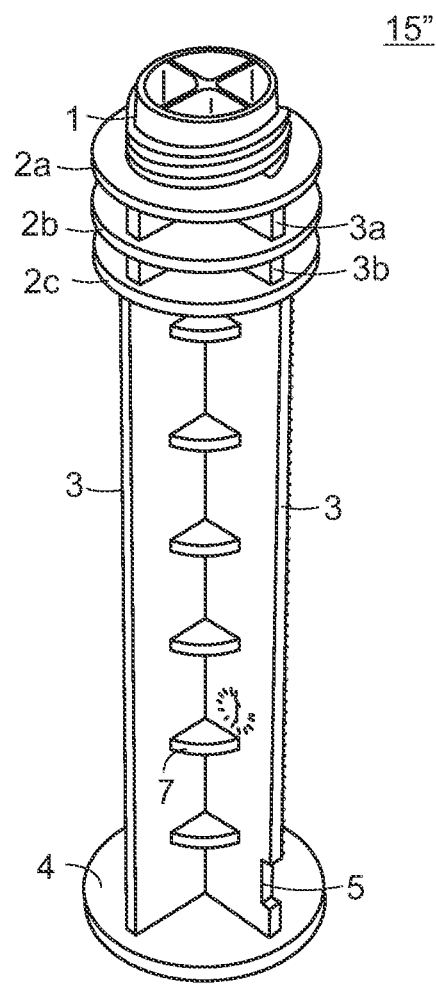
FIG. 2.c

PLUNGER ROD COMPRISING AT LEAST THREE ANNULAR ELEMENTS FOR A PREFILLED SYRINGE

CROSS REFERENCE TO RELATED APPLICATIONS

This application is a continuation of U.S. application Ser. No. 15/555,220, filed Sep. 1, 2017, now U.S. Pat. No. 10,543,319, which is a U.S. national stage application of International Application no. PCT/EP2016/054351, filed Mar. 2, 2016, which claims the benefit of the filing date of European Application No. 15000587.4, filed Mar. 2, 2015, the contents of which are hereby incorporated by reference in their entirety.

The invention relates to a plunger rod for a syringe body prefilled with a medical fluid and to a syringe including the plunger rod and the syringe body prefilled with the medical fluid.

WO 2014/053560 A1 discloses a syringe prefilled with a medical fluid. In one embodiment, the plunger rod and the syringe body are mounted located side by side in an over pack. To use the syringe, the plunger rod and the syringe body have first to be removed out of the over pack. The plunger rod is then screwed into the plunger closing the rear end of the syringe body. The content of the named patent application is incorporated fully into the present patent application by reference.

The object underlying the invention is to provide an improved plunger rod. The inserting, in particular the screwing, of the plunger rod into the plunger is to be improved. In particular, leakage caused by tilting the plunger is to be avoided where possible. In addition, the guiding of the plunger rod in the syringe body is to be improved, in particular when using the syringe in a syringe pump.

Said object is achieved by the subject matter with the features according to the independent claims. Advantageous embodiments are the object of the dependent claims, the description and the drawings.

The prefilled syringe according to the invention includes the following component parts: a syringe body which is filled with a medical fluid and comprises on a front end a nozzle, which is closed by way of a cap, and which is closed on a rear end by way of a displaceable plunger, and a plunger rod which is insertable into the syringe body via the rear end and comprises on a front end a connecting portion, by means of which the plunger rod is connectable to the plunger, wherein at least three annular elements, which extend at least in portions about a longitudinal axis of the plunger rod, are arranged on the plunger rod on a rear end of the connecting portion such that when the plunger rod is fully connected to the plunger, they are situated in the syringe body. The syringe, in this case, is in its initial state. I.e. the plunger has not yet been moved to eject the fluid.

The three annular elements support a coaxial connection between the plunger rod and the plunger. The annular elements prove advantageous, on the one hand, as they prevent tilting over the entire circumference of 360°. On the other hand, the three annular elements make it possible for the user, when connecting the plunger rod to the plunger, to have haptic and/or acoustic control. If, for example, the user connects the plunger rod correctly to the plunger immediately, he does not receive a haptic and/or acoustic message. If, for example, in contrast, the user tries, unintentionally, to connect the plunger rod incorrectly askew, he is able to perceive, in particular, the transition of the plunger rod from the central annular element to the rear annular element on the edge of the rear syringe body opening as a type of jump, preferably connected to a type of click. As a result, the user is able to recognize that he is trying to connect the plunger rod incorrectly to the plunger and can then correct the position of the plunger rod in a corresponding manner.

The position of the plunger in the prefilled syringe body and the position of the three annular elements on the plunger rod are matched to one another such that in a first step, when the plunger rod is placed by way of its connecting portion on the plunger, the two front rings are already arranged in the interior of the syringe body. When connecting, for example screwing-in, the plunger rod is initially guided through the two front annular elements. The rear third ring supports the guiding of the plunger rod when the plunger rod is finally, fixedly connected to the plunger.

The three annular elements are positioned in the interior of the syringe body no later than in the state in which the plunger rod is fully connected to the plunger, preferably is screwed into the plunger.

According to a first embodiment, an outside diameter of the three annular elements is identical to an inside diameter of the syringe body or is somewhat smaller than an inside diameter of the syringe body. As a result, the three annular elements can be guided on an inner side of the syringe body when connecting the plunger rod to the plunger and later when moving the plunger for ejecting the fluid. The outside diameter of the three annular elements is preferably identical.

In a further embodiment, wing elements or ribs, which extend radially outwardly, are arranged distributed over the circumference of the plunger rods, preferably individually, between the annular elements. The wing elements preferably connect the annular elements together. The wing elements are proved to be advantageous as they enable guidance in a longer, in portions continuous manner along the longitudinal axis of the plunger rod.

In one design, at least four wing elements are arranged preferably at an angle of 90° with respect to one another, in particular individually, between the annular elements. Guidance that is as coaxial as possible is to be supported as a result. The wing elements preferably comprise an outside diameter which is identical to the inside diameter of the syringe body or is somewhat smaller than the inside diameter of the syringe body. In a first embodiment, the wing elements comprise a diameter which is identical to the outside diameter of the annular elements. The guidance of the plunger rod is improved even more as a result. In a second embodiment, the wing elements comprise an outside diameter which is smaller than an outside diameter of the annular elements. The haptic and/or acoustic control is improved as a result when the plunger rod is connected to the plunger and/or when the plunger rod is inserted into the syringe body. In one design, the outside diameter of the wing elements is reduced in relation to the outside diameter of the annular elements by between 1 mm and 10 mm, preferably by between 4 mm and 8 mm.

The prefilled syringe can be provided, for example, in an over pack. If, for example, the medical fluid is oxygen-sensitive and the syringe body is not sufficiently oxygen-impermeable, the syringe can be packaged in an oxygen-impermeable over pack, for example in a blister. The plunger rod can already be premounted, for example, on the plunger. However, it can also not be premounted and be located next to the syringe body in the over pack. Consequently, within the field of the invention is also an over pack having an interior in which the afore-described syringe according to the invention is enclosed.

In addition, within the field of the invention is also the plunger rod, in particular for a or for the aforementioned prefilled syringe. The plunger rod includes a front-end connecting portion, by means of which the plunger rod is connectable to the plunger. In this case, at least three annular elements, which extend at least in portions about a longitudinal axis of the plunger rod, are arranged on a rear end of the connecting portion. The three annular elements, preferably individually, are arranged at a distance R with respect to one another, where 0.5 mm≤R≤20 mm, in a preferred manner 1 mm≤R≤10 mm and particularly preferred 2 mm≤R≤8 mm. The annular elements have, for example, a thickness of approximately between 0.5 mm and approximately 5 mm, preferably between approximately 1 mm and approximately 3 mm. The plunger rod has a diameter D where 8 mm≤D≤30 mm and/or a length L where 80 mm≤L≤150 mm.

In addition, a syringe is also claimed, including a syringe body, a plunger and the afore-described plunger rod, wherein the plunger is positionable in the syringe body in such a manner and the three annular elements are arranged on the plunger rod in such a manner that, when the plunger rod is fully connected to the plunger, they are situated in the syringe body. The syringe body is preferably prefilled with a medical fluid.

The prefilled syringe can have, for example, a holding volume of between 5 ml and 100 ml. The medical fluid can be or include, for example, a fluid for enteral and/or parenteral nutrition and/or for infusion. The medical fluid can be provided by a solution and/or by an emulsion. The medical fluid can also include medical substances. According to one embodiment, the medical fluid is or includes the medicinal fluid Propofol, in particular a Propofol emulsion. Propofol is described by the chemical name 2,6-diisopropylphenol (IUPAC).

The syringe body can be molded from plastics material, which includes one of the following polymers: cyclo-olefin copolymer, cyclo-olefin polymer or crystal clear polymer. Such a plastics material container is resistant to solvents. In particular, such a plastics material container can be used to store Propofol which acts as a solvent. The outer sides of the plunger and/or the inner side of the syringe body are preferably coated at least in portions with a lubricant, preferably are siliconized.

According to one embodiment, the plastics material plunger rod is molded from plastics material which preferably includes one of the following polymers: cyclo-olefin copolymer, cyclo-olefin polymer or crystal clear polymer, or it is molded from polypropylene.

Figure 4:
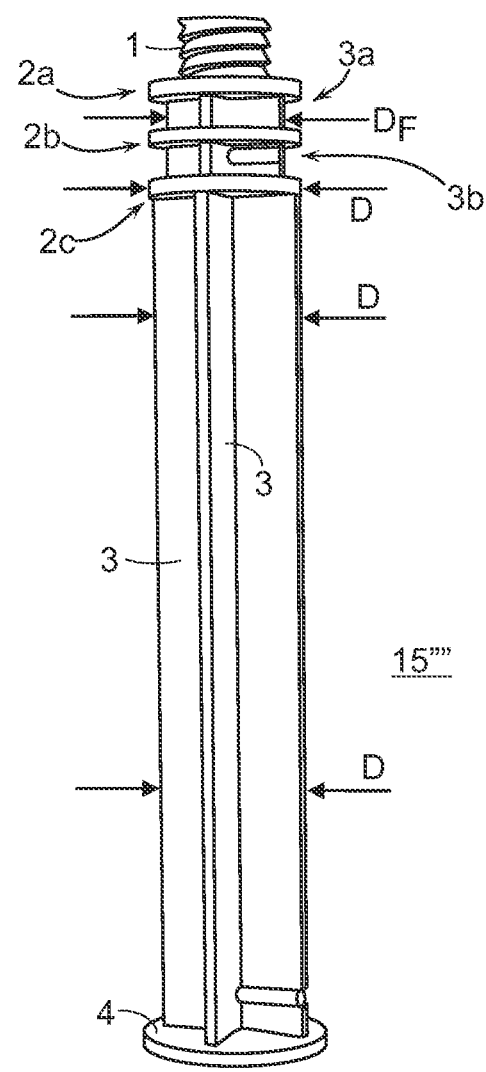

The invention is described in detail below by way of exemplary embodiments in connection with the drawings, in which:

FIG. 1.*a* shows a side view of a plunger rod according to a first embodiment of the invention;

FIG. 1.*b* shows a side view of a prefilled syringe according to the invention with the plunger rod from FIG. 1.*a*;

FIG. 2.*a* shows a side view of a plunger rod according to a second embodiment of the invention;

FIG. 2.*b* shows a side view of a prefilled syringe according to the invention with the plunger rod from FIG. 2.*a*;

FIG. 2.*c* shows a perspective view of the plunger rod according to the second embodiment of the invention from FIG. 2.*a*;

FIG. 3 shows a perspective view of a plunger rod according to a third embodiment of the invention and FIG. 4 shows a perspective view of a plunger rod according to a fourth embodiment of the invention.

FIG. 1.*a* shows a plunger rod 15' according to a first embodiment of the invention. The plunger rod 15' has a substantially cross-shaped cross section and is formed by the two legs 3. Stabilizing elements 7 are mounted along the longitudinal axis. The rear end of the plunger rod 15' is closed off by a flange 4 with a larger diameter. The notches 5 provided on the rear end enable the plunger rod 15' (as a component part of the syringe 20) to be operated in a syringe pump. The plunger rod 15' is designed for operation in a syringe 20 with a holding volume of between approximately 50 ml and 70 ml. A graduation 6 to 50 ml is provided on the plunger rod 15'. The plunger rod 15' has a diameter D where 25 mm≤D≤30 mm and/or a length L where 100 mm≤L≤150 mm.

The front end of the plunger rod 15' is provided by a connecting portion 1, by means of which the plunger rod 15' is connected to a plunger 12, not shown here, (see FIG. 1.*b* in this respect). The connecting portion 1 is provided here, as an example, by a screw thread. Three annular elements 2*a*, 2*b*, 2*c* connect to the rear end of the connecting portion 1. As a result, when the plunger rod 15'' is screwed into the plunger 12, it is possible, in particular, for the user to have haptic and/or acoustic control. The annular elements 2*a*, 2*b*, 2*c* preferably extend over the entire circumference of the plunger 15'. The front annular element 2*a* additionally forms the stop when the plunger rod 15' is screwed into the plunger 12. The three annular elements 2*a*, 2*b*, 2*c* are preferably arranged equidistantly with respect to one another. In one embodiment, the three annular elements 2*a*, 2*b*, 2*c* are arranged individually at a distance R of between 2 mm and 8 mm with respect to one another. The annular elements 2*a*, 2*b*, 2*c* have for example, a thickness of approximately between 0.5 mm and approximately 5 mm, preferably of approximately between 1 mm and approximately 3 mm.

The cross-shaped cross section of the plunger rod 15' is also continued between the three annular elements 2*a*, 2*b*, 2*c*. Ignoring the flange 4 and the connecting portion 1, the diameter D of the plunger rod is identical or substantially identical along the longitudinal axis. As a result, so-called wing elements 3*a*, 3*b* or ribs are formed between the three annular elements 2*a*, 2*b*, 2*c*. The front, here four, wing elements 3*a* connect the front ring 2*a* to the central ring 2*b*. The rear, here four, wing elements 3*b* connect the central ring 2*b* to the rear ring 2*b*. The annular elements 2*a*, 2*b*, 2*c* and the wing elements 3*a*, 3*b* enable the plunger rod 15' to be guided into the syringe body 8 in as coaxial a manner as possible and, as a result, enable the plunger rod 15' to be screwed into the plunger 12 in as coaxial a manner as possible (see FIG. 1.*b* in this respect). Placing the plunger rod 15' on the plunger 12 at an angle, leading to possible tilting of the plunger 12 and finally possibly to resultant leakage can be reduced or even avoided as a result.

FIG. 1.*b* illustrates the use of the plunger rod 15' from FIG. 1.*a* in a prefilled syringe 20. The syringe 20 includes a syringe body 8 with a nozzle 9 arranged on the front end of the syringe body 8, a cap 11 closing the nozzle 9, a plunger 12 which is arranged in the syringe body 8 and closes the interior of the syringe body 8 in a fluid-tight manner, and the plunger rod 15' from FIG. 1*a* which is connected to the plunger 12 by means of its connecting portion 1. The connection between the plunger 12 and the plunger rod 15' is provided here by means of a screw connection. A thread, which is, however, not shown in the figure, is also provided in a corresponding manner in the interior of the plunger 12.

The outside diameter D or $D_F$ of the plunger rod 15' and/or of the annular elements 2*a*, 2*b*, 2*c* and/or of the wing elements 3*a*, 3*b* can be identical to the inside diameter of the syringe body 8. In order to make it easier for the plunger rod 15' to move in the syringe body 8, the outside diameter D or $D_F$ of the plunger rod 15' and/or of the annular elements 2a, 2b, 2c and/or of the wing elements 3a, 3b is, in particular, smaller than the inside diameter of the syringe body 8. The outside diameter D or $D_F$ is preferably reduced in relation to the inside diameter of the syringe body 8 by approximately between 0.5 mm and 5 mm.

The prefilled syringe 20 can be filled, for example, via its initially open rear end and then can be closed by way of the plunger 12. The plunger rod 15' can then be connected to the plunger 12 at a later point in time, for example shortly before the application. However, the plunger 12 can also, for example, be inserted into the syringe body 8 with the plunger rod 15' already screwed into the plunger 12.

The position of the plunger 12 in the prefilled syringe body 8 and the position of the three annular elements 2a, 2b, 2c on the plunger rod 15' are preferably matched to one another in such a manner that in a first step, when the plunger rod 15' is placed on the plunger 12 by way of its connecting portion 1, the two front rings 2a, 2b are already arranged in the interior of the syringe body 8 and are preferably guided by the inner side of the syringe body 8. When being screwed in, the plunger rod 15' is initially guided by the two front annular elements 2a, 2b and the front wing elements 3a and then also by the rear wing elements 3b in the syringe body 8. The rear third ring 2c supports the guiding of the plunger rod 15' in the final, fixed connection between the plunger rod 15' and the plunger 12. The three rings 2a, 2b, 2c are positioned in the interior of the syringe body 8 no later than in the state in which the plunger rod 15' is fully connected to the plunger 12, preferably is screwed into the plunger 12. The annular elements 2a, 2b, 2c prove to be advantageous as they prevent tilting over the entire circumference of 360°. The wing elements 3a, 3b prove to be advantageous as they enable longer guidance along the longitudinal axis of the plunger rod 15'. The present invention joins said advantages together.

FIGS. 2.a to 2.c show a plunger rod 15" according to a second embodiment of the invention. Only the differences to the plunger rod 15' from FIG. 1.a are explained below. For all the other components, reference is made to the preceding description concerning FIG. 1.a. The plunger rod 15" does not have a graduation. In contrast to the embodiment shown in FIG. 1.a, the wing elements 3a, 3b, which connect the three annular elements 2a, 2b, 2c together, do not have the identical outside diameter as the three annular elements 2a, 2b, 2c. The outside diameter $D_F$ of the wing elements 3a, 3b is smaller than the outside diameter D of the three annular elements 2a, 2b, 2c. The outside diameter $D_F$ of the wing elements 3a, 3b is preferably reduced by approximately between 4 mm and 8 mm in relation to the outside diameter D of the annular elements 2a, 2b, 2c. In the present case, there are precisely three annular elements which are located in the front region of the plunger rod 15'.

As a result, when screwing the plunger rod 15" into the plunger 12, it is possible, in particular, for the user to have haptic and/or acoustic control. If the user screws the plunger rod 15" correctly into the plunger 12 immediately, he does not receive a haptic and/or acoustic message. If, in contrast, the user tries, unintentionally, to screw the plunger rod 15" into the plunger 12 incorrectly askew, he is able to perceive, in particular, the transition of the plunger rod 15" from the central annular element 2b to the rear annular element 2c on the edge 14 in the rear syringe body opening (see FIG. 2.b in this respect) as a type of jump, preferably connected to a type of click. As a result, the user is able to recognize that he is trying to connect the plunger rod 15" incorrectly to the plunger 12 and then he can correct the position of the plunger rod 15" in a corresponding manner.

In addition, FIG. 3 shows a plunger rod 15''' according to a third embodiment of the invention. The design of said plunger rod 15''' corresponds substantially to the design of the plunger rod 15" from FIGS. 2.a to 2.c. The present plunger rod 15''' simply comprises different dimensions as it is designed for a syringe 20 with a holding volume of between approximately 20 ml and 30 ml. The plunger rod 15''' has a diameter D where 13 mm≤D≤23 mm and/or a length L where 100 mm≤L≤150 mm. The distance R between the annular elements here is also 2 mm≤R≤8 mm.

Finally, FIG. 4 shows a plunger rod 15'''' according to a fourth embodiment of the invention. The design of said plunger rod 15'''' corresponds substantially to the design of the plunger rods 15" and 15''' from FIGS. 2.a to 2.c and 3. The present plunger rod 15'''' simply comprises different dimensions as it is designed for a syringe 20 with a holding volume of between approximately 10 ml and 15 ml. The plunger rod 15'''' has a diameter D where 8 mm≤D≤18 mm and/or a length L where 80 mm≤L≤110 mm. The distance R between the annular elements here is 2 mm≤R≤8 mm. In addition, no stabilizing elements 7 are provided on the plunger rod 15'''.

It is clear to the person skilled in the art that the described embodiments are to be understood as examples. The invention is not limited to said embodiments but can be varied in many different ways without departing from the essence of the invention. Features of individual embodiments and the features named in the general part of the description can be combined with one another both individually and together.

The invention claimed is:
1. A prefilled syringe comprising
a syringe body which is filled with a medical fluid and comprises, on a front end thereof, a nozzle, which is closed by way of a cap, wherein the syringe body is closed, on a rear end thereof, by way of a displaceable plunger, and
a plunger rod, which is insertable into the syringe body via the rear end of the syringe body and comprises, on a front end thereof, a connecting portion by means of which the plunger rod is connectable to the plunger,
wherein at least three annular elements extend along a portion of a longitudinal axis of the plunger rod, the portion being next to a rear end of the connecting portion,
wherein the portion extends from a proximal-most annular element to a distal-most annular element,
wherein, when the connecting portion of the plunger rod is fully connected to the plunger, the at least three annular elements are situated in the syringe body,
wherein the annular elements engage the syringe body to promote maintenance of a coaxial position of the plunger rod relative to the plunger while the connecting portion is being connected to the plunger,
wherein wing elements, extend radially outwardly and connect the at least three annular elements together, the wing elements being distributed along a circumference of the plunger rod,
wherein an outside diameter ($D_F$) of the wing elements within the portion along which the three annular elements extend is smaller than an outside diameter (D) of the at least three annular elements, and
wherein the rear end of the plunger rod is closed off by a flange.

2. The prefilled syringe as claimed in claim 1, wherein a position of the plunger in the prefilled syringe body and the position of the at least three annular elements on the plunger rod are matched to one another such that in a first step, when the plunger rod is placed by way of its connecting portion on the plunger, two of the at least three annular elements are arranged in the interior of the syringe body.

3. The prefilled syringe as claimed in claim 2, wherein the outside diameter (D) of the at least three annular elements and an inside diameter of the syringe body are selected to enable the at least three annular elements to engage the syringe body.

4. The prefilled syringe as claimed in claim 2, wherein the outside diameter (D) of the at least three annular elements is identical.

5. The prefilled syringe as claimed in claim 2, wherein at least four wing elements are arranged to form angles therebetween, each angle being 90°, wherein the at least four of the wing elements are arranged between two of the at least three annular elements.

6. The prefilled syringe as claimed in claim 1, wherein the outside diameter (D) of the at least three annular elements and an inside diameter of the syringe body are selected to enable the at least three annular elements to engage the syringe body to permit guiding the plunger rod in the syringe body.

7. The prefilled syringe as claimed in claim 1, wherein the outside diameter (D) of the at least three annular elements is identical.

8. The prefilled syringe as claimed in claim 1, wherein at least four of the wing elements are arranged, to form angles therebetween, each angle being 90°, wherein the at least four of the wing elements are arranged between two of the at least three annular elements.

9. The prefilled syringe as claimed in claim 1, wherein the outside diameter ($D_F$) of the wing elements is selected to enable the wing elements to engage the syringe body.

10. The prefilled syringe as claimed in claim 1, wherein the outside diameter ($D_F$) of the wing elements is substantially the same as the outside diameter (D) of the at least three annular elements.

11. The prefilled syringe as claimed in claim 1, wherein the outside diameter ($D_F$) of the wing elements is less than the outside diameter (D) of the at least three annular elements by between 1 mm and 10 mm.

12. The prefilled syringe as claimed in claim 1, wherein the plunger rod is premounted on the plunger.

13. The prefilled syringe as claimed in claim 1, wherein the plunger rod is located next to the syringe body in an oxygen-impermeable, over pack.

14. An oxygen-impermeable over pack having an interior in which the syringe as claimed in claim 1, wherein it is hermetically enclosed.

15. A plunger rod for a prefilled syringe as claimed in claim 1, including a front-end connecting portion, the plunger rod being connectable to a plunger, wherein the at least three annular elements, extend at least in portions about a longitudinal axis of the plunger rod and are arranged at a distance R, wherein 0.5 mm≤R≤20 mm.

16. A pre-filled syringe as claimed in claim 1, the prefilled syringe including a plunger positionable in the syringe body and the at least three annular elements are arranged on the plunger rod such that, when the plunger rod is fully connected to the plunger, the at least three annular elements are situated in the syringe body.

17. The prefilled syringe as claimed in claim 1, wherein the wing elements are individually arranged between the at least three annular elements.

18. The prefilled syringe as claimed in claim 1, wherein the outside diameter ($D_F$) of the wing elements is less than the outside diameter (D) of the at least three annular elements by between 4 mm and 8 mm.

19. A plunger rod for a prefilled syringe as claimed claim 1, including a front-end connecting portion, the plunger rod being connectable to a plunger, wherein the at least three annular elements extend at least in portions about a longitudinal axis of the plunger rod and are arranged at a distance R, wherein 1 mm≤R≤10 mm.

20. An oxygen-impermeable overpack comprising:
a prefilled syringe and a plunger rod; wherein the prefilled syringe and the plunger rod are hermetically enclosed within an interior of the oxygen impermeable overpack;
the plunger rod including a front-end connecting portion by means of which the plunger rod is connectable to a plunger, wherein at least three annular elements which extend at least in portions about a longitudinal axis of the plunger rod and which are arranged on a rear end of the connecting portion at a distance R, wherein 0.5 mm≤R≤20 mm,
wherein wing elements, extend radially outwardly and connect the at least three annular elements together, the wing elements being arranged distributed over a circumference of the plunger rod, an outside diameter ($D_F$) of the wing elements is smaller than an outside diameter (D) of the at least three annular elements,
wherein the rear end of the plunger rod is closed off by a flange.

21. A plunger rod for a prefilled syringe, the plunger rod comprising a front end connecting portion, by means of which the plunger rod is connectable to a plunger, wherein at least three annular elements which extend at least in portions about a longitudinal axis of the plunger rod and which are arranged on a rear end of the connecting portion at a distance R, wherein 0.5 mm≤R≤20 mm, wherein wing elements, extend radially outwardly and connect the at least three annular elements together, the wing elements being arranged distributed over a circumference of the plunger rod, an outside diameter ($D_F$) of the wing elements is smaller than an outside diameter (D) of the at least three annular elements, wherein the rear end of the plunger rod is closed off by a flange.

22. A prefilled syringe comprising
a syringe body having a front end and a rear end, said syringe body being filled with a medical fluid,
a displaceable plunger that closes said body at said rear end,
a nozzle at said front end,
a cap that closes said nozzle, and
a plunger rod that is insertable into said syringe body at said rear end thereof,
wherein said plunger rod that extends along a longitudinal axis, said plunger rod comprising
wing elements distributed along a circumference of said plunger rod and extending radially outward from said longitudinal axis,
a connecting portion that is configured to connect to said displaceable plunger at said rear end, and
three annular elements that extend along a portion of said longitudinal axis, said portion being next to a rear end of said connecting portion, said portion extending from a proximal-most annular element to a distal-most annular element, said three annular elements being connected to each other by said wing elements, wherein, when said connecting portion of said plunger rod is fully connected to said displaceable plunger, said three annular elements are situated in said syringe body, wherein the annular elements engage the syringe body to promote maintenance of a coaxial position of the plunger rod relative to the plunger while the connecting portion is being screwed into the plunger, wherein an outside diameter of the wing elements within the portion along which the three annular elements extend is smaller than an outside diameter of the at least three annular elements, and wherein the rear end of the plunger rod is closed off by a flange.

* * * * *